United States Patent
Belk et al.

(10) Patent No.: US 8,644,923 B2
(45) Date of Patent: Feb. 4, 2014

(54) DETERMINATION OF UPPER LIMIT OF VULNERABILITY USING A VARIABLE NUMBER OF SHOCKS

(75) Inventors: Paul A. Belk, Maple Grove, MN (US); Charles D. Swerdlow, Los Angeles, CA (US); Linda L. Ruetz, New Brighton, MN (US)

(73) Assignees: Medtronic, Inc., Minneapolis, MN (US); Imperception, Inc., Los Angeles, CA (US)

( * ) Notice: Subject to any disclaimer, the term of this patent is extended or adjusted under 35 U.S.C. 154(b) by 1083 days.

(21) Appl. No.: 12/178,903

(22) Filed: Jul. 24, 2008

(65) Prior Publication Data

US 2010/0023073 A1    Jan. 28, 2010

(51) Int. Cl.
*A61N 1/365*    (2006.01)

(52) U.S. Cl.
USPC ............................................................ 607/4

(58) Field of Classification Search
USPC ............................................. 607/2, 4, 17–18
See application file for complete search history.

(56) References Cited

U.S. PATENT DOCUMENTS

| | | | |
|---|---|---|---|
| 5,000,189 A | 3/1991 | Throne et al. | |
| 5,105,809 A | 4/1992 | Bach, Jr. et al. | |
| 5,346,506 A | 9/1994 | Mower et al. | |
| 5,564,422 A | 10/1996 | Chen et al. | |
| 5,954,753 A | 9/1999 | Alt et al. | |
| 6,477,422 B1 | 11/2002 | Splett | |
| 6,675,042 B2 | 1/2004 | Swerdlow et al. | |
| 7,181,275 B2 | 2/2007 | Havel | |
| 7,181,285 B2 | 2/2007 | Lindh et al. | |
| 7,257,441 B2 | 8/2007 | Swerdlow et al. | |
| 2003/0195569 A1 | 10/2003 | Swerdlow et al. | |
| 2004/0111120 A1* | 6/2004 | Sarkar et al. | 607/5 |
| 2004/0220631 A1 | 11/2004 | Burnes et al. | |
| 2005/0038478 A1 | 2/2005 | Klepfer et al. | |
| 2005/0065555 A1* | 3/2005 | Er | 607/4 |
| 2006/0235476 A1 | 10/2006 | Gunderson et al. | |
| 2008/0033494 A1* | 2/2008 | Swerdlow | 607/5 |
| 2008/0269813 A1* | 10/2008 | Greenhut et al. | 607/5 |
| 2009/0093860 A1 | 4/2009 | Belk et al. | |

FOREIGN PATENT DOCUMENTS

| | | |
|---|---|---|
| EP | 0536873 A1 | 4/1993 |
| EP | 0597431 A2 | 5/1994 |
| WO | 2004024231 A1 | 3/2004 |
| WO | 2004026398 A1 | 4/2004 |
| WO | 2004098704 A1 | 11/2004 |
| WO | 2006115940 A1 | 11/2006 |
| WO | 2009045610 A1 | 4/2009 |

OTHER PUBLICATIONS

Response to Rule 161(1) EPC communication from counterpart European Patent Application No. 09790716.6 dated Nov. 30, 2011 (8 pages).

(Continued)

*Primary Examiner* — George Manuel
*Assistant Examiner* — Minh Duc Pham
(74) *Attorney, Agent, or Firm* — Shumaker & Sieffert, P.A.

(57) ABSTRACT

A method and apparatus sense a cardiac electrical signal and determine a signal quality parameter of the cardiac electrical signal. A number of shock pulses to be delivered to a patient's heart is determined in response to the signal quality parameter. Each of the shock pulses are scheduled to be delivered at a unique offset from a T-wave shock interval in one embodiment of the invention.

21 Claims, 8 Drawing Sheets

(56) References Cited

OTHER PUBLICATIONS

Amendment in response to Office Action from U.S. Appl. No. 12/178,850, dated Dec. 30, 2011 filed on Mar. 30, 2012 (13 pages).
Office Action from related U.S. Appl. No. 12/178,850 dated Dec. 30, 2011 (10 pages).
Non-Final Office Action from U.S. Appl. No. 11/866,700 dated Mar. 14, 2011 (9 pages).
Response to Non-Final Office Action from U.S. Appl. No. 11/866,700, filed Jun. 14, 2011 (13 pages).
Office Action from U.S. Appl. No. 12/178,850 dated Jul. 6, 2012 (9 pages).
Office Action from related U.S. Appl. No. 12/178,850 dated Jan. 24. 2013 (9 pages).
Reply to European Office Action from corresponding European Application No. 09790711.7 filed on Dec. 13, 2012 (6 pages).
European Exam Report from corresponding European Application Serial No. 09 790 711.7-2305 dated Jul. 10, 2012 (5 pages).
Shehata, M. et al; "Automatic Determination of Timing Intervals for Upper Limit of Vulnerability Using ICD Electrograms"; PACE—Pacing and Clinical Electrophysiology; Blackwell Futura Publishing; vol. 31, Jun. 2008; pp. 691-700.
Response in response to final Office Action dated Jul. 6, 2012 from U.S. Appl. No. 12/178,850, filed Sep. 7, 2012 (6 pages).
Advisory Action dated Sep. 19, 2012 from U.S. Appl. No. 12/178,850 (3 pages).
Pre-Appeal Brief Request for Review in response to Advisory Action dated Sep. 19, 2012 from U.S. Appl. No. 12/178,850, filed Nov. 6, 2012 (4 pages).
Shehata, M. et al; "Automatic Determination of Timing Intervals for Upper Limit of Vulnerability Using ICD Electrograms"; Pace-Pacing and Clinical Electrophysiology; Blackwell Futura Publishing; vol. 31, Jun. 2008; pp. 691-700.
PCT International Search Report; PCT/US2009/051366.

* cited by examiner

DETERMINATION OF UPPER LIMIT OF VULNERABILITY USING A VARIABLE NUMBER OF SHOCKS

TECHNICAL FIELD

The invention relates generally to implantable medical devices and, in particular, to an automated method for controlling T-wave shock delivery.

BACKGROUND

Delivery of a shock pulse during the vulnerable period of the cardiac cycle can induce fibrillation, providing the shock energy is greater than a patient-specific minimum value and less than a patient-specific maximum value. Such a shock pulse is generally referred to as a "T-shock" or "T-wave shock" because the time of the vulnerable period during the cardiac cycle generally corresponds to the T-wave of the ECG signal. The upper limit of vulnerability (ULV) for an individual patient is the shock strength at or above which fibrillation is not induced when a shock is delivered during the vulnerable period of a normal cardiac cycle. The minimum shock strength required to defibrillate the human heart, often referred to as the defibrillation threshold (DFT), corresponds quantitatively to the ULV.

In past practice, patients receiving an implantable cardioverter defibrillator (ICD) have undergone DFT testing in order to ensure a reasonable certainty of successful defibrillation using shock pulse energies below the maximum output capacity of the ICD. The DFT has been determined by inducing fibrillation through delivery of a shock during the T-wave, then delivering defibrillation shocks to verify successful defibrillation at shock energies at least a safety margin below the maximum ICD output.

Determination of the ULV as a surrogate for DFT affords the opportunity to significantly reduce the number of times needed to induce fibrillation in a patient in order to ensure the patient's DFT falls below the maximum ICD output. The ULV, which can be measured in regular rhythm, corresponds to a shock strength that defibrillates with a high probability of success.

However, a challenge remains in determining the proper timing of a T-shock delivered to determine the ULV. If a T-shock is properly timed during the vulnerable period, and is greater than or equal to the ULV, fibrillation will not be induced. However, if a T-shock that is below the ULV is delivered just outside the vulnerable period, the resultant failure to induce fibrillation may lead to an incorrect determination of the ULV. Correct timing of T-shocks during the vulnerable period can be determined using 12-lead ECG signals by manually measuring the time interval between a test pacing pulse and a selected point on the T-wave. The ICD is then programmed to deliver a shock at that time interval. However, such techniques using 12-lead ECG signals are time-consuming and require considerable skill. A need remains, therefore, for automated methods for applying shocks at appropriate times relative to the T-wave for reliable ULV determination and DFT estimation.

DETAILED DESCRIPTION

Figure 1:
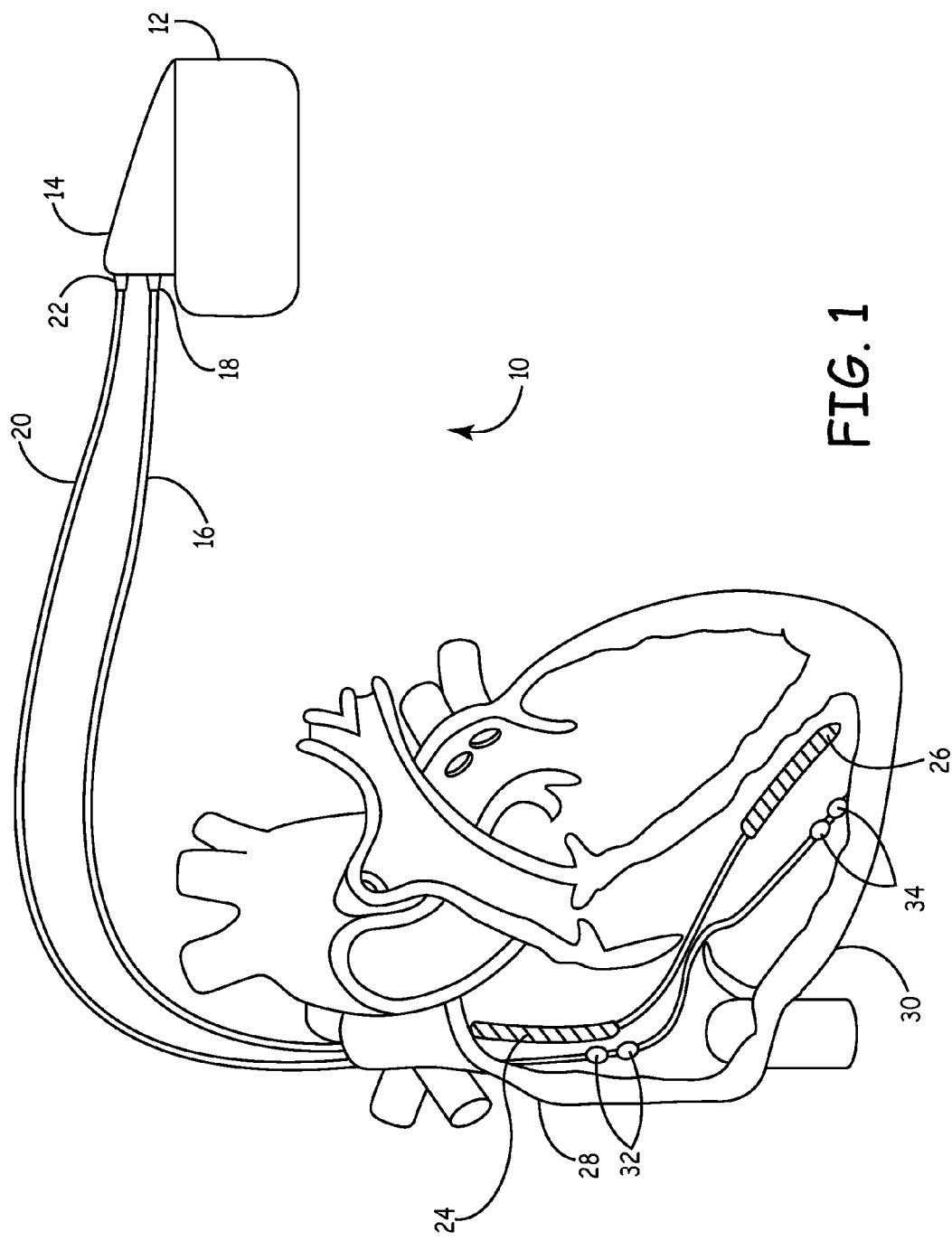
FIG. 1 is a plan view of an ICD coupled to a patient's heart via intracardial leads according to one embodiment of the present invention.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a plan view of an ICD coupled to a patient's heart via intracardial leads according to one embodiment of the present invention. ICD 10 includes a housing 12 for enclosing circuitry within ICD 10 and a connector block 14 for receiving an electrical connector 18 of high-voltage lead 16 and electrical connector 22 of pacing/sensing lead 20. High-voltage lead 16 carries a proximal coil electrode 24 and a distal coil electrode 26. High-voltage lead 16 is shown configured to position proximal electrode 24 along the right atrium 28 and/or along the superior vena cava (SVC) and position distal electrode 26 within right ventricle (RV) 30. Proximal electrode 24 is referred to hereafter as an "SVC coil electrode", and distal electrode 26 is referred to hereafter as "RV coil electrode". Alternatively, these two electrodes may be on different leads. SVC coil electrode 24, RV coil electrode 26 and the housing 12 of ICD 10 may be used in any combination for delivering a high-voltage shock pulse. A shock pulse may be delivered for determining the ULV or DFT at ICD implantation or follow-up or for delivering a defibrillation shock in response to detecting fibrillation.

Pacing/sensing lead 20, carries two sets of pacing/sensing electrodes, a proximal electrode set 32 positioned within the right atrium 28 and a distal electrode set 34 positioned within the right ventricle 30. Alternatively, electrode sets 32 and 34 may be on different leads or on the lead that carries either or both coil electrodes 24 and 26. As another alternative, separate electrode pairs may be used for right-ventricular pacing and sensing. In various embodiments of the invention, the leads, electrodes for delivering high-voltage shock pulses and electrodes for pacing and sensing may be intracardiac, epicardial, intravascular, subcutaneous or submuscular designs.

Because DFTs vary with electrode placement and lead configuration, as well as with the responsiveness of a particular patient's heart, the ULV is determined after the electrodes and leads have been placed at their intended implant positions. In this manner, the ULV corresponds to the patient and particular arrangement of the electrodes used.

Figure 2:
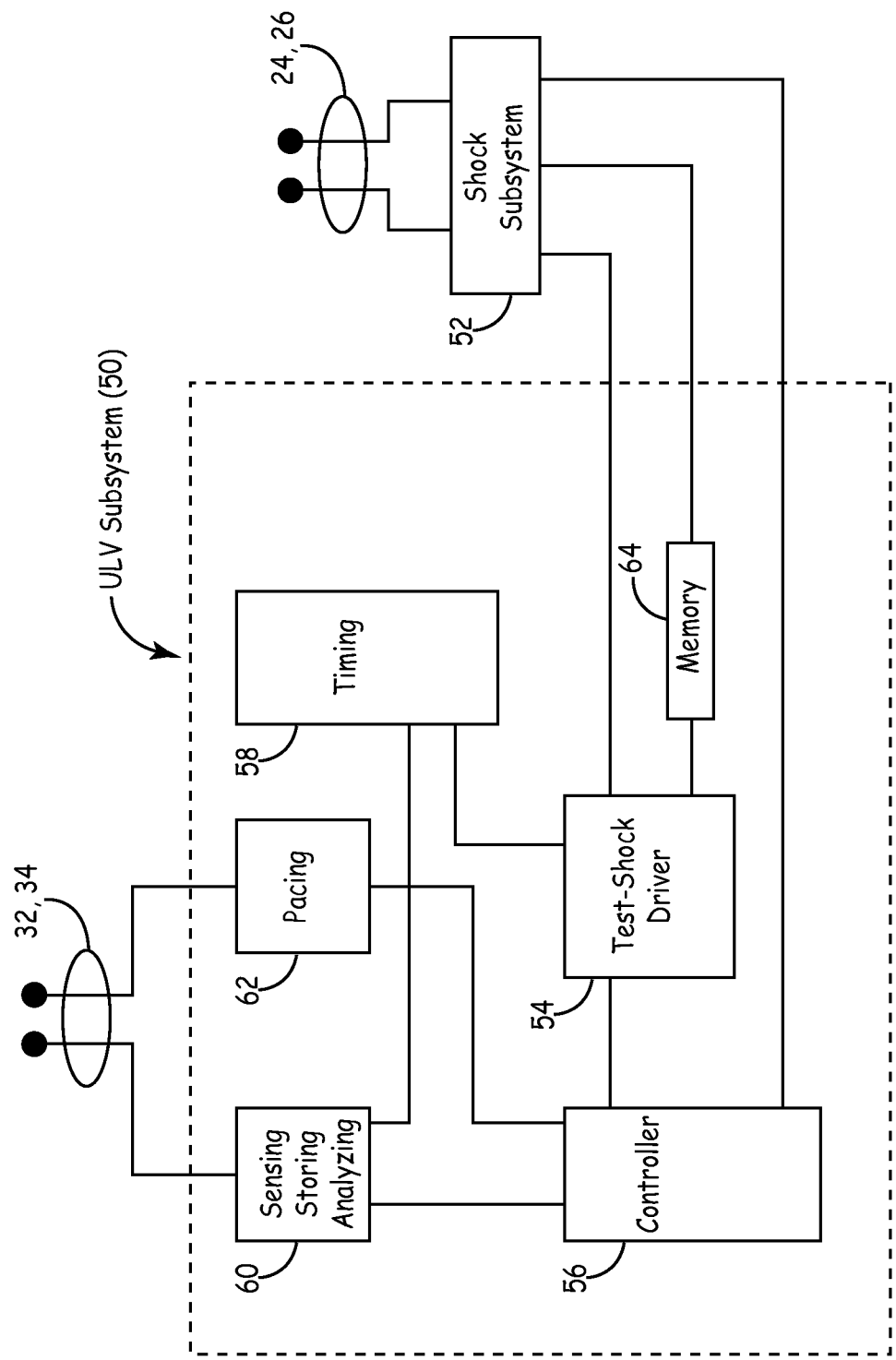
FIG. 2 is a functional block diagram of one embodiment of a ULV subsystem in electrical connection with a shock subsystem.

FIG. 2 is a functional block diagram of one embodiment of a ULV subsystem 50 in electrical connection with a shock subsystem 52. ULV subsystem 50 and shock subsystem 52 are component subsystems of ICD 10 of FIG. 1 and are enclosed within housing 12 and electrically connected with other ICD circuitry and with ICD leads or electrodes as appropriate to achieve the desired functionality as described herein. ULV subsystem 50 includes a test-shock driver 54 for triggering T-wave shocks to be generated by shock subsystem 52. A control module 56 in combination with memory unit 64 and timing circuit 58 control test shock driver 54 and pacing circuit 62. A sensing, storing, and analyzing circuit 60 is provided for sensing, storing, and analyzing cardiac electrogram (EGM) signals.

Shock subsystem 52 is programmable to deliver monophasic or biphasic shocks, having variable tilt, and controllable through a stepwise range of energy outputs from, for example, at least 5 J to at least 30 J. When shock subsystem 52 is included in a subcutaneous ICD system relying on subcutaneous electrodes for defibrillating the heart, the output range may be substantially higher. Shock subsystem 52 is connected to the test shock driver 54, memory 64 and control module 56 of the ULV subsystem 50. Shock subsystem 52 is used to generate test shock pulses used in determining the ULV for a patient as well as generate defibrillation shocks in response to ICD detection of tachycardia or fibrillation.

ULV measurement techniques described herein are generally performed during cardiac pacing delivered by pacing circuit 62 under the control of timing circuit 58 at a rate slightly higher than an intrinsic heart rate determined by sensing, storing and analyzing circuit 60. Alternatively, pacing pulses may be delivered at a predetermined high rate, for example 120 bpm, expected to be above the patient's resting heart rate. The pacing circuit 62, however, is not necessary for embodiments of the invention which are operative during an intrinsic rhythm.

Control module 56 is set to control the delivery of pacing and shock delivery, providing an initial test-shock energy, and triggering sensing circuit 60 to detect the heart's intrinsic rate and transmit this rate value back to control module 56. The starting shock strength is stored in memory unit 64. The intrinsic heart rate value is passed to pacing circuit 62. Pacing circuit 62 then provides a baseline pacing output to electrode sets 32, 34 that is of a rate sufficient to overdrive the heart's intrinsic rate. The sensing, storing, and analyzing circuit 60 then evaluates an EGM signal, which represents the electrical activity of the heart.

The timing of pacing pulses may be transmitted to the sensing circuit 60 electronically. Alternatively, the sensing, storing, and analyzing circuit 60 may identify the pacing pulse during its evaluation of the EGM. EGM signals received by sensing, storing and analyzing circuit 60 may include signals sensed using a number of different configurations of implanted electrodes including, but not limited to, intracardiac, transvenous, epicardial, intravascular, subcutaneous, and submuscular leads. Examples of sensing lead combinations may include leads positioned to record signals from the superior vena cava, the right atrium, the right ventricle, the left ventricle and combinations of electrodes such as between a lead tip electrode and a defibrillation electrode or combinations including pairing leads from the right atrium or the superior vena cava to the right or left ventricles.

A series of ventricular pacing pulses, such as 8-15 pulses, are delivered at an overdrive pacing rate. As will be described in greater detail herein, the sensing, storing and analyzing circuit 60 senses the EGM signals following at least some of the pacing pulses and evaluates the T-waves to determine a selected fiducial point of the T-wave. In various embodiments, the fiducial point may be a T-wave peak or a peak derivative or slope of the T-wave. The time interval between the pacing pulse and the fiducial point will be used in setting a T-wave shock interval for controlling the time of delivery of a T-wave shock for determining or estimating the patient's ULV.

The test shock driver 54 in cooperation with control module 56 and timing circuitry 58 operates to trigger shock subsystem 52 to deliver a number of T-shocks delivered relative to the set T-wave shock time interval. Each T-wave shock is delivered at a unique offset relative to the determined T-wave shock interval. Multiple T-wave shocks are delivered in order to "scan" the T-wave to ensure at least one shock pulse coincides with the vulnerable period and promote reliable ULV estimation. As will be further described herein, the controller 56 will set the number of T-wave shocks to be delivered based on an analysis of the T-wave signal quality during delivery of a pacing pulse series. The selected number of T-wave shocks are delivered according to multiple offsets, which may be stored in memory 64 or computed by controller 56 as a function of the T-wave signal quality and/or T-wave shock interval.

Figure 3A:
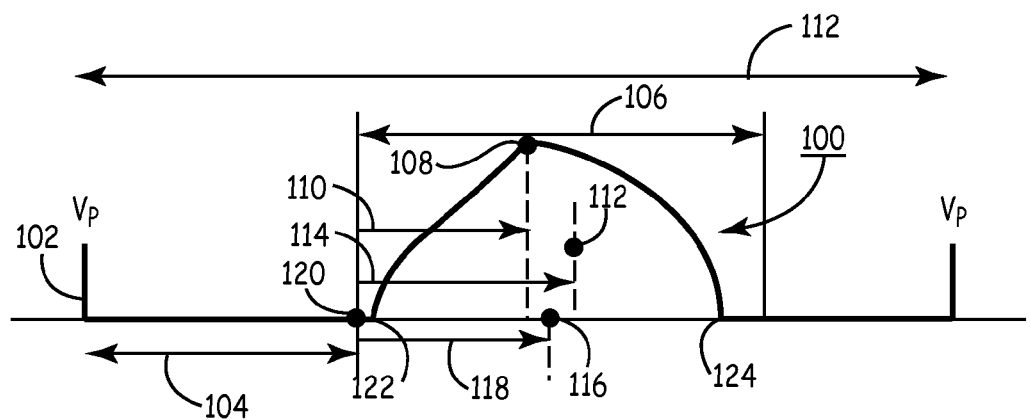
FIG. 3A is a diagram of a differentially filtered T-wave signal sensed following a pacing pulse illustrating several fiducial points that may be used for computing a T-wave shock time interval.

FIG. 3A is a diagram of a differentially filtered T-wave signal 100 sensed following a pacing pulse 102 illustrating several fiducial points that may be used for computing a T-wave shock time interval. The ULV subsystem 50 delivers a pacing pulse 102 at a desired pacing interval 112. A blanking period 104 is applied following the pacing pulse 102. A T-wave sensing window 106 is initiated at the end of the blanking period 104 to enable sensing of the T-wave signal 100 during the sensing window 106. The T-wave signal 100 is analyzed by control module 56 to determine a signal quality parameter. A signal quality parameter may be determined using a characteristic of the T-wave signal such as frequency content, total area, number of peaks, number of zero crossings, or other characteristics. The signal quality parameter may be compared to a predefined acceptable threshold or range to determine an indication of the stability and reliability of the T-wave signal. Alternatively, the signal quality parameter may be compared between consecutive or non-consecutive T-wave signals to determine a stability of the signal quality parameter.

In other embodiments, the signal quality parameter is determined based on the stability of a fiducial point identified from the T-wave signal 100. A fiducial point may be defined as any feature of the T-wave signal 100 identified through signal analysis. One fiducial point that may be identified is a signal peak 108, as generally disclosed in U.S. Pat. No. 6,675, 042 (Swerdlow, et al.), hereby incorporated herein by reference in its entirety. Another fiducial point that may be identified is a T-wave center of area 112 or a T-wave center of width 116 as generally disclosed in U.S. patent application Ser. No. 12/178,850, filed Jul. 24, 2008, which published as U.S. Patent Application Publication No. 2010/0023072 on January 28, 2010, and which is hereby incorporated herein by reference in its entirety.

The T-wave peak 108 may be identified using peak detection techniques and may be identified using a filtered T-wave, which may include differential filtering, or a T-wave signal derivative as disclosed in the above-incorporated '042 patent. The T-wave center of area 112 may be determined by computing a weighted sum of T-wave signal sample points and dividing by the sum of the T-wave signal sample points. The T-wave center of width 116 may be determined by searching in the T-wave sensing window 106 for a first zero crossing 122, occurring prior to signal peak 108, and a second zero crossing 124, occurring after signal peak 108, and determining the midway point 116 between the first and second zero crossings. In other embodiments, fiducial points may be determined as a magnitude or time of a signal peak, peak derivative, inflection point, signal area or a time of a zero-crossing.

The magnitude and/or the time of occurrence of a fiducial point with respect to a reference time point may be compared between consecutive or non-consecutive cardiac cycles to determine the stability of the fiducial point as in indication of T-wave signal quality. In one embodiment, the fiducial point is identified and used to determine a time interval between the start of the T-wave sensing window 120 and a time point corresponding to the fiducial point. For example a time interval 110 may be identified between T-wave sensing window start 120 and the T-wave signal peak 108. A time interval 114 may be identified between T-wave sensing window start 120 and T-wave center of area 112. Alternatively or additionally, time interval 118 may be determined between T-wave sensing window start 120 and T-wave center width 116. Any of these time intervals 110, 114 and 118 may be used as a signal quality parameter or used in computing a signal quality parameter. For example, a time interval 110, 114, or 118 determined for one T-wave signal may be compared to a similarly determined time interval for another T-wave signal occurring earlier or later than the first T-wave signal.

Any of the time intervals 110, 114 and 118 may further be used to set a T-wave shock interval. A test shock interval may be computed as the sum of the blanking interval 104 and a selected fiducial point time interval 110, 114 or 118. The test shock interval may be used in computing a T-wave shock interval used in controlling the delivery of a T-wave shock for inducing ventricular fibrillation. The T-wave shock interval may be computed as an average, median, maximum, minimum or other function of a multiple measured test shock intervals.

It is recognized that a T-wave signal characteristic, fiducial point amplitude, or time interval relating to a fiducial point may be computed for multiple T-wave signals such that a signal quality parameter may be computed based on a variation of any of the T-wave signal characteristics or features. Likewise, the final T-wave shock interval may be computed based on multiple fiducial point time interval measurements. As will be further described herein, a number of T-wave shocks to be delivered at time points relative to a computed T-wave shock interval may be determined based on the signal quality parameter. Each of the T-wave shocks may be delivered at a unique offset relative to the T-wave shock interval. The offset may be a fixed interval or a percentage of the T-wave shock interval.

Figure 3B:
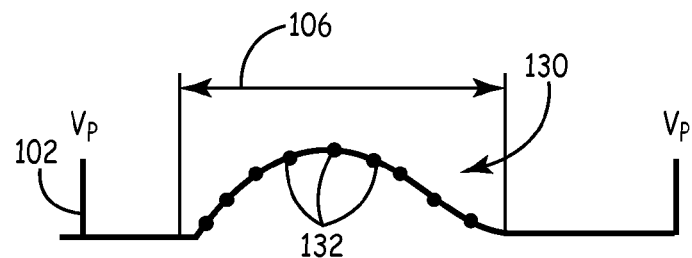
FIG. 3B is a diagram of a differentially filtered T-wave signal sensed following a pacing pulse illustrating an alternative signal quality assessment.

FIG. 3B is a diagram of a differentially filtered T-wave signal 130 sensed following a pacing pulse 102 illustrating an alternative signal quality assessment. In some situations, the differentially filtered T-wave signal 130 may have a relatively wide and flat morphology that precludes reliable identification of a signal peak as a fiducial point. Multiple, substantially equal peaks 132 may be detected by a peak detection algorithm. As such, if the ULV subsystem is relying on signal peak detection for determining a T-wave shock interval, the accuracy of the T-wave shock interval in matching the vulnerable period may be compromised when the peak detection algorithm has difficulty identifying a single maximum peak.

Accordingly, in some embodiments of the invention, a signal quality parameter used in selecting the number of T-wave shocks may relate to the signal morphology as it pertains to reliable and accurate identification of a targeted fiducial point. The particular T-wave signal morphology may make fiducial point detection difficult or inconsistent from beat-to beat, even if the signal morphology itself is consistent from beat-to-beat and relatively noise free. As such, a signal quality parameter may be defined as a T-wave signal morphology parameter that is an indication of the reliability of fiducial point determination.

In the example shown in FIG. 3B, morphology parameters that may be determined as a signal quality parameter for the purposes of setting a number of T-wave shocks include the number of maximum peaks and the difference in amplitude between an identified maximum peak and its neighboring sample points. If multiple peaks 132 are found or if the difference in amplitude between an identified peak and its neighboring sample points is less than a predetermined threshold, the accuracy of maximum peak detection for setting T-wave shock interval determination may be limited. The number of T-wave shocks delivered is increased in response to such identification in order to promote the certainty of shock delivery during the patient's vulnerable period.

Another example of a T-wave signal morphology parameter that may be determined as a signal quality parameter for use in setting a number of T-wave shocks is a ratio of signal amplitude to signal width. A relatively low, flat differentially-filtered T-wave signal, as generally shown in FIG. 3B, may result in an identified maximum peak being within a short time interval, for example 20 to 30 ms, of similar values and indicate less reliable fiducial point identification for the purposes of setting a T-wave shock interval corresponding to the vulnerable period. As such, a greater number of T-wave shocks may be scheduled to promote certainty of delivering of a shock during the vulnerable period.

In yet another embodiment, a T-wave signal morphology parameter may be measured as the difference between a signal peak and neighboring sample points occurring over a predetermined interval surrounding the signal peak. If the difference is within a baseline noise amplitude range, the reliability of fiducial point detection in setting a T-wave shock interval may be limited. For example, if the baseline noise is approximately 0.1 mV/sec for a differentially-filtered T-wave signal and the amplitudes of a majority of sample points within a 30 ms interval of an identified signal peak are less than 0.1 mV/sec different than the identified signal peak, the confidence in detecting the correct signal peak as the fiducial point is reduced. A greater number of T-wave shocks may be scheduled in response to this reduced confidence.

It is recognized that numerous morphology-based parameters may be defined as a signal quality parameter as they pertain to the confidence in detecting a fiducial point used in setting a T-wave shock interval. The morphology-based parameter will be defined depending on the particular fiducial point sought. The morphology based parameter may be determined using the T-wave signal, a differentially-filtered T-wave signal or after performing other signal conditioning that may or may not be performed when the fiducial point itself is being detected. It is recognized that one having skill in the art and the benefit of the teachings provided herein may conceive of numerous variations of morphology parameters indicative of the reliability of fiducial point detection for use as a signal quality parameter used to set a variable number of T-wave shocks.

Figure 4:
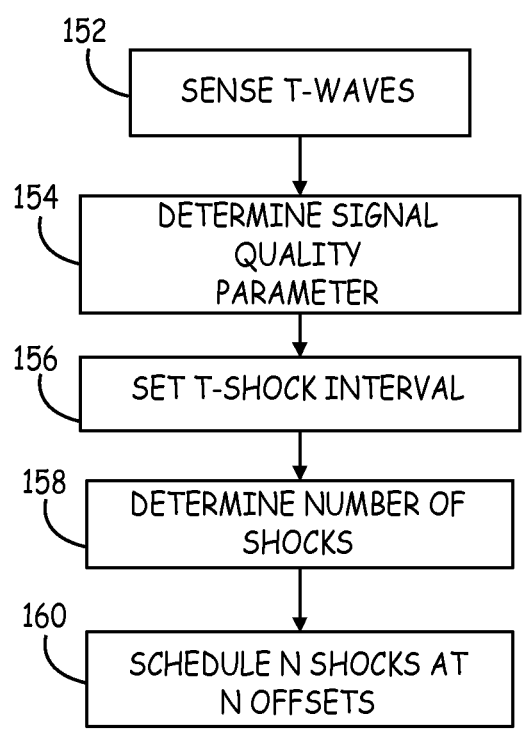
FIG. 4 is a flow chart of a method for delivering a T-wave shock for use in estimating a patient's defibrillation threshold.

FIG. 4 is a flow chart of a method for delivering a T-wave shock for use in estimating a patient's defibrillation threshold. A T-wave shock interval computed using the methods described herein is useful in any application requiring shock pulse delivery during the vulnerable period, which includes ULV and DFT measurement or estimation. Flow chart 150 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software, firmware, or hardware or any combination thereof to accomplish the present invention in the context of any modern ICD, given the disclosure herein, is within the abilities of one of skill in the art.

Methods described in conjunction with flow charts and diagrams presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 152, cardiac electrical signals including T-wave signals are sensed for performing a signal quality analysis. Cardiac electrical signals may be sensed using any implanted electrodes, e.g. intracardiac, epicardial, transvenous, subcutaneous, or submuscular electrodes, and may include sensing signals using external ECG electrodes.

At block 154, the T-wave signals sensed during a T-wave sensing window are analyzed to determine a signal quality parameter. The signal quality parameter may be determined as a characteristic or feature of the T-wave signal, an amplitude or time interval associated with a fiducial point identified from the T-wave signal, or as a morphology parameter indicative of the reliability of fiducial point detection as described above. At block 156 a T-shock interval is set. A fiducial point used in determining the signal quality parameter at block 154 may be used in setting the T-shock interval.

At block 158, a number of shocks to be delivered to the patient is determined based on the signal quality parameter determined at block 154. The signal quality parameter may be compared to a predetermined threshold or comparisons may be made between individual beats to determine stability of the T-wave signal. In one embodiment, a test shock interval corresponding to a fiducial point on the T-wave is determined for at least two cardiac cycles, which may be consecutive or non-consecutive cardiac cycles. The difference between at least two test shock intervals based on the identified fiducial point is determined. The difference or variability between the test shock intervals is used to determine the number of T-wave shocks that are delivered during ULV testing. A greater number of T-wave shocks are delivered in response to poorer signal quality, or greater variability in measured test shock intervals. By delivering a greater number of T-wave shocks spread out over the T-wave at different offsets relative to a computed T-wave shock interval, the likelihood of missing the vulnerable period during ULV or defibrillation threshold testing is reduced.

For example, in one embodiment, if the difference between test shock intervals determined for two cardiac cycles based on time intervals corresponding to a T-wave signal fiducial point is less than a predetermined signal quality threshold, for example 40 ms, a nominal number of T-shock pulses, e.g., six T-shock pulses, may be selected to be delivered to the patient's heart at a corresponding number of different offsets relative to a final T-shock interval. The final T-shock interval may be an average, median, minimum, maximum, or other function of the measured test shock intervals. The offsets may be positive or negative relative to the final T-shock interval and may include a zero offset. In one embodiment, T-shocks are delivered at +20 ms, +40 ms, +60 ms, 0 ms, −20 ms, and −40 ms relative to a T-shock interval. The T-shock interval may be based on a T-wave center of area, center of width, a signal peak, and/or another fiducial point of the T-wave signal.

If the difference between the test shock intervals is greater than the signal quality threshold, a greater number of T-shock pulses, for example eight T-shock pulses, is selected to be delivered to the patient's heart at a like number of different offsets relative to the T-shock interval.

The selected number of T-shocks is scheduled at block 160 according to offsets stored in memory. Typically each T-shock is delivered at the scheduled interval, i.e. the T-shock interval set based on measured test shock intervals plus a predetermined offset, following the last pulse of a pacing pulse series.

Figure 5:
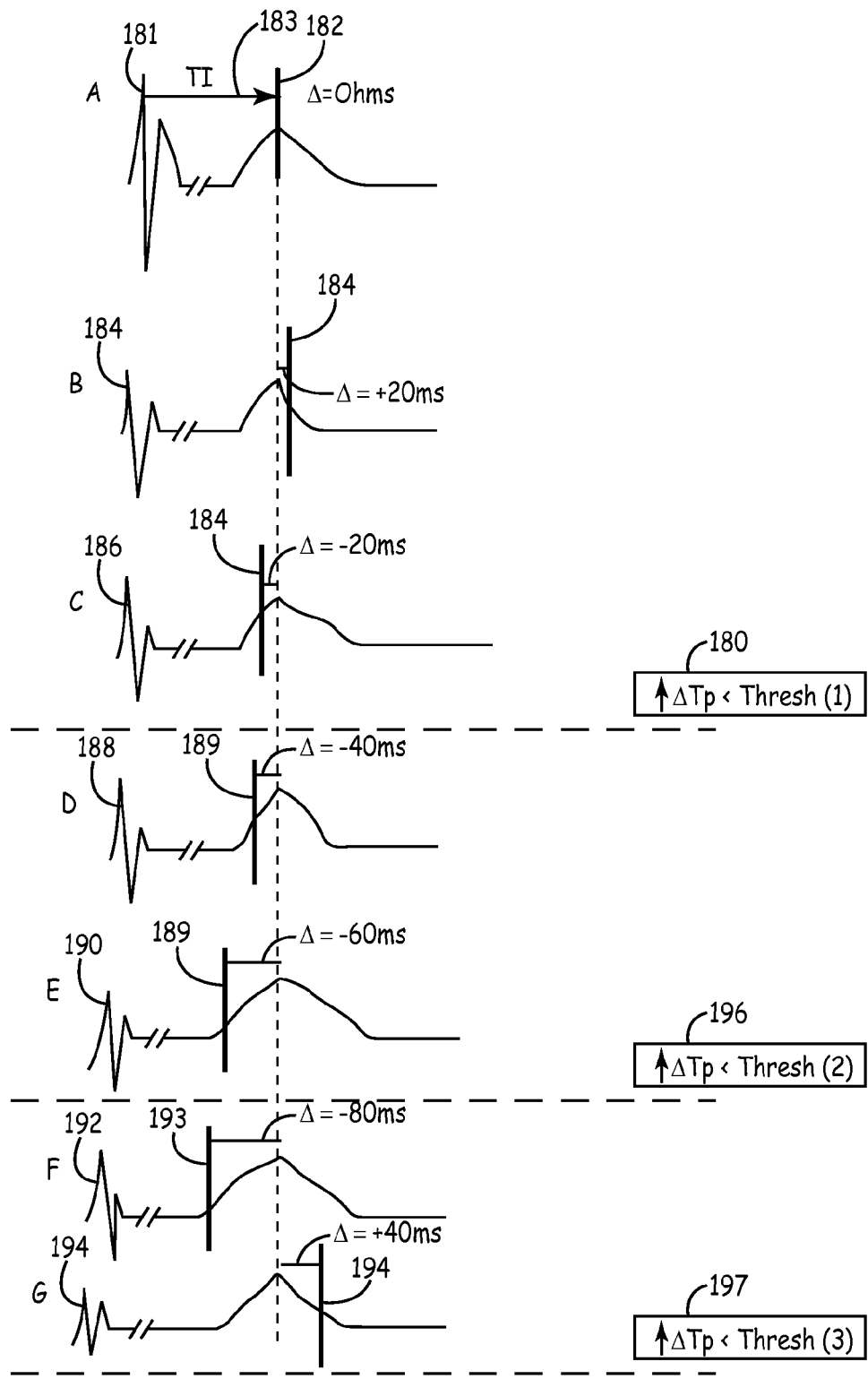
FIG. 5 is a diagram of selected numbers of T-wave shocks delivered at varying offsets relative to a computed T-shock interval.

FIG. 5 is a diagram of selected numbers of T-wave shocks delivered at varying offsets relative to a computed T-shock interval. A tiered signal quality threshold may be defined to allow selection of a variable number of shocks depending on the signal quality. For example, thresholds relating to the variability of a time interval associated with a fiducial T-wave signal point may be set corresponding to high, moderate, and low signal quality.

In the example, of FIG. 5, three signal quality threshold levels are implemented. The T-wave signal quality parameter is computed as the difference between time intervals, $\Delta T_p$, corresponding to a T-wave signal fiducial point. $\Delta T_p$ is compared to three threshold levels, Thresh(1), Thresh(2) and Thresh (3). If $\Delta T_p$ is less than Thresh(1) as determined at block 180, indicating high signal quality or stability in the T-wave signals, three T-shocks 182, 185 and 187 are delivered. The three T-shocks are scheduled to be delivered at three different offsets relative to the computed T-shock interval (TI) 183 following the last pacing pulse 181, 184, and 186 of three different series of pacing pulses A, B, and C, respectively.

Following the last pacing pulse 181 of pacing series A, the first T-shock 182 is delivered at a 0 ms offset relative to the T-shock interval (TI) 183. The second T-shock 185 is delivered at a +20 ms offset relative to the T-shock interval 183 following the last pulse 184 of a second pacing pulse series B. The third T-shock 187 is delivered at a −20 ms offset relative to the T-shock interval 183 following the last pulse 186 of a third pacing pulse series C.

If the signal quality parameter $\Delta T_p$ is greater than Thresh (1) but less than Thresh(2), as determined at block 196, indicating a moderate T-wave signal quality or stability, five T-shocks are scheduled to be delivered. In addition to the first 3 shocks 182, 185 and 187 delivered at offsets of 0 ms, +20 ms, and −20 ms, respectively, a fourth T-shock 189 is delivered at a −40 ms offset and a fifth T-shock 191 is delivered at a −60 ms offset. Accordingly, a fourth pacing pulse series D is delivered with a final pacing pulse 188 preceding the fourth T-wave shock 189. A fifth pacing pulse series E having a final pacing pulse 190 is followed by the fifth T-wave shock 191.

If the signal quality parameter $\Delta T_p$ is greater than Thresh(2) but less than Thresh(3), as determined at block 197, indicating a low but still acceptable T-wave signal quality or stability, seven T-wave shocks are scheduled to be delivered. In addition to T-shocks 182, 185, 187, 189, and 191, a sixth T-wave shock 193 is delivered at a −80 ms offset relative to the T-shock interval 183 following the last pacing pulse 192 of a sixth pacing pulse series F. A seventh T-wave shock 195 is delivered at a +40 ms offset relative to the T-shock interval 183 following the last pacing pulse 194 of a seventh pacing pulse series G.

If the signal quality parameter $\Delta T_p$ is greater than Thresh (3), the T-wave signal quality or stability is deemed unacceptable. The ULV or DFT testing may be aborted or a new T-shock interval may be computed.

Figure 6:
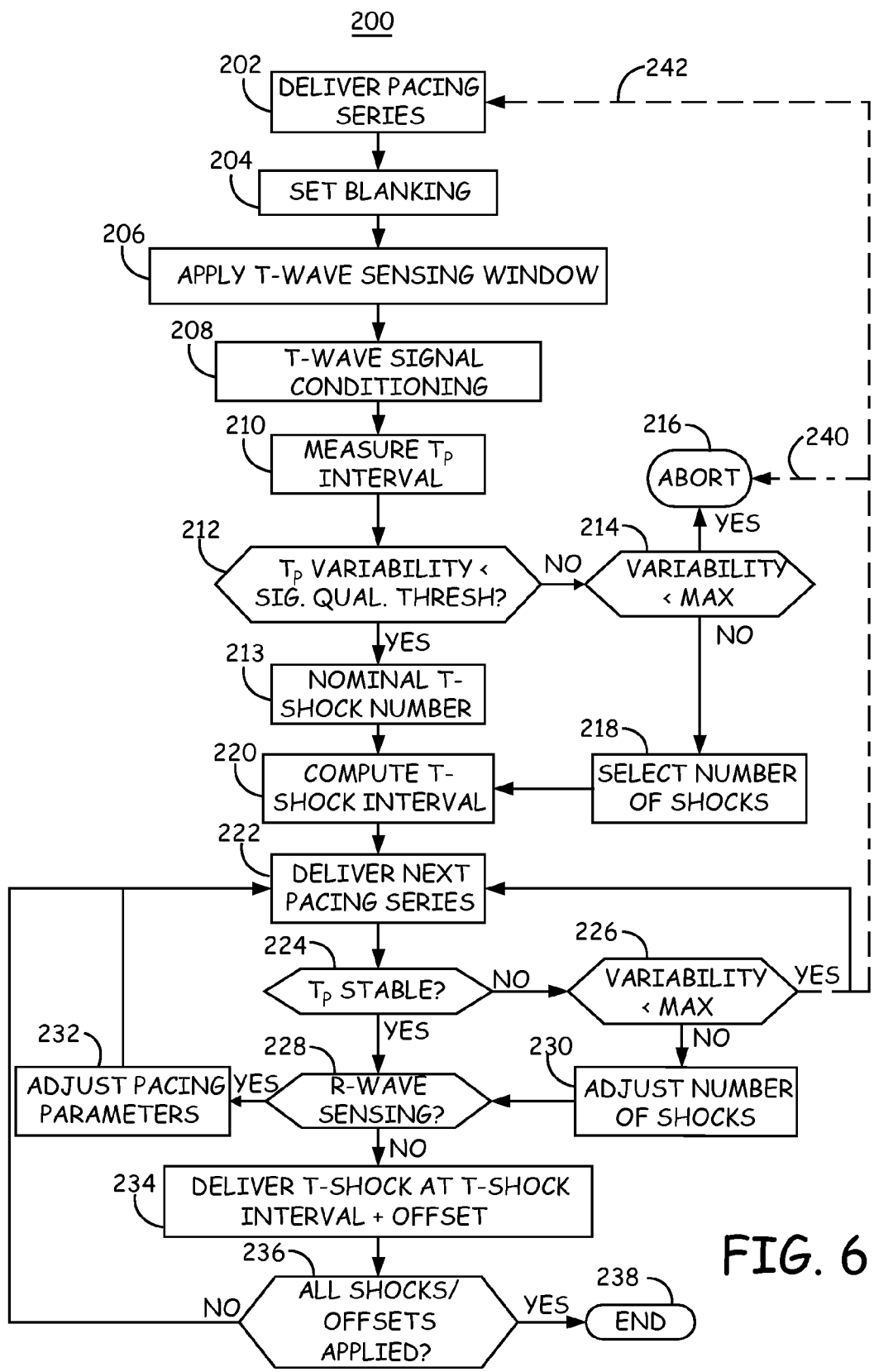
FIG. 6 is a flow chart of a method for controlling a variable number of T-wave shocks based on a T-wave signal quality parameter.

FIG. 6 is a flow chart of a method 200 for controlling a variable number of T-wave shocks based on a T-wave signal quality parameter. At block 202 a series of pacing pulses is delivered to allow measurement of T-wave signal quality parameter and for computing a T-shock interval. Typically a series of 6 to 10 pacing pulses are delivered at 500 ms intervals or at another rate greater than the patient's intrinsic heart rate. A blanking period is applied at block 204 following each pacing pulse. A T-wave sensing window is applied at block 206 immediately following each blanking period to allow T-wave signal analysis. T-wave signal sensing may be performed using any available sensing electrode configuration. With reference to FIG. 1, T-wave signal sensing may be performed using the RV coil electrode 26 to the combination of the SVC coil electrode 24 and housing 12.

At block 208 the sensed T-wave signal is filtered and may undergo additional signal conditioning processes. For example, filtering may include band pass, low pass and differential filtering. In one embodiment, the EGM signal is band pass filtered at 3 to 100 Hz. The T-wave signal is further low pass filtered using a 12 Hz Butterworth filter. Signal filtering may include determining a T-wave signal time derivative and using the time derivative for identifying a fiducial T-wave signal point and measuring a test shock interval corresponding to the fiducial T-wave signal point. In one embodiment, differential filtering is performed using a five-point differential filtering method. In various embodiments, different filtering methods may be used for reducing high frequency noise.

Additional signal conditioning performed at block 208 may include detecting the peak of the filtered T-wave signal and using the peak polarity for correcting signal sample points having the opposite polarity of the peak. In other words, if the maximum amplitude of the T-wave signal is a positive value, indicating a positive-going T-wave, all negative T-wave signal sample points are reset to zero. If the maximum T-wave amplitude is a negative value, indicating a negative-going T-wave, all positive T-wave signal sample points are set to zero. In this way, noisy sample points having opposite polarity from the T-wave polarity are removed.

At block 210, a time interval, $T_p$ interval, associated with a fiducial T-wave signal point, $T_p$, is measured with respect to the start time of the T-wave sensing window. The $T_p$ interval is determined for one or more of the T-wave signals following the pacing pulses. The $T_p$ interval may be determined based on a differentially-filtered T-wave signal peak, the center of the T-wave area, the center of the T-wave width, or any other selected fiducial T-wave signal point. The $T_p$ interval may be computed using a filtered T-wave signal, using differential filtered T-wave signal, or using T-wave signal sample points that have undergone other signal conditioning.

At block 212, a signal quality check is performed to verify that the $T_p$ intervals measured for individual T-wave signals are stable. The signal quality check includes comparing two or more individually measured $T_p$ intervals to determine a difference or variability between $T_p$ intervals. In one embodiment, the difference between two $T_p$ intervals is compared to a signal quality threshold. For example, during a series of eight ventricular pacing pulses, the difference between the $T_p$ intervals measured for the seventh and eighth pacing cycles is compared to a signal quality threshold of 40 ms. If the $T_p$ interval variability is less than the signal quality threshold, indicating stable and reliable T-wave signals, a nominal number of T-wave shocks is selected at block 213. A T-shock interval is computed at block 220 using the computed $T_p$ intervals during the first pacing pulse series. The T-shock interval may be computed using a percentage, average or median value of one or more $T_p$ interval measurements. In one embodiment, the T-wave shock interval is computed as the blanking period plus an average of the $T_p$ intervals determined for the seventh and eight differentially-filtered T-wave signals measured during a series of eight pacing pulses.

It is recognized that numerous methods may be implemented to verify the reliability of $T_p$ interval measurements. Such methods may include determining a standard deviation of $T_p$ intervals or performing cross-checks between individual measurements or between individual measurements and an average of all individual measurements. The signal quality threshold will be defined according to the methods used for computing the signal quality parameter, or $T_p$ interval in this example. Furthermore, it is recognized that any combination of T-wave features may be determined for comparisons of T-wave signals for verifying the signal quality of the sensed T-wave signals.

The signal quality check performed at block 212 may further include performing capture verification for ensuring that T-wave measurements are made following pacing pulses that consistently capture the heart. A loss of capture during a pacing pulse series can produce anomalous test shock interval measurements and result in an inappropriate T-wave shock interval. Capture verification may be performed by monitoring for an evoked response (QRS complex) during the blanking period following a pacing pulse. Capture verification methods are generally disclosed, for example, in U.S. Pat. No. 6,466,422 (Splett), hereby incorporated herein by reference in its entirety.

The signal quality check performed at block 212 may also include sensing for intrinsic R-waves occurring between pacing pulses. As will be further described below, sensed R-waves occurring during the pacing pulse series will result in an irregular heart rhythm making $T_p$ interval measurements unreliable. The $T_p$ interval measurements may be discarded when R-waves are sensed during the first pacing pulse series. Method 200 may be aborted at block 216 and may be repeated, immediately or after a delay, by returning to block 202.

If the variability between $T_p$ intervals is greater than the signal quality threshold at block 212, the variability may be compared to a maximum acceptable variability at block 214. If the $T_p$ interval variability exceeds a maximum acceptable threshold or other rejection criteria are met, such as intrinsic R-wave sensing or loss of capture, the T-wave signal quality or stability is deemed unreliable. The method 200 may be aborted at block 216. Method 200 may be repeated a desired number of attempts either immediately or at a later time by returning to block 202.

If the $T_p$ interval variability does not exceed a maximum signal quality threshold, and no other rejection criteria are met, as determined at block 214, a number of T-shocks is selected at block 218 based on the level of the $T_p$ interval variability. As described in conjunction with FIG. 5, the $T_p$ interval variability may be compared to one or signal quality thresholds in selecting a variable number of T-wave shocks. After selecting the number of T-wave shocks to be delivered, the T-wave shock interval is computed at block 220 based on the measured $T_p$ intervals as described above.

Once the T-shock interval is computed at block 220, a next series of pacing pulses is delivered at block 222. A stability verification may be performed at block 224 to verify that the cardiac rhythm has remained stable in terms of the $T_p$ interval variability. For example, $T_p$ interval measurements may be repeated on a subset (or all) of the EGM signals sensed following the pacing pulses of the next pacing series using the same methods used at block 212 for determining a $T_p$ interval variability. The $T_p$ interval measurements may be compared to the $T_p$ interval measurements used for computing the T-shock interval, compared to the computed T-shock interval itself, or used to compute a new T-shock interval that is compared to the T-shock interval computed at block 220. If any of these comparisons result in a stability threshold being exceeded at block 224, the $T_p$ interval variability determined for the second series of pacing pulses is compared to a maximum signal quality threshold at block 226. If the maximum signal quality threshold is exceeded, method 200 may return to block 222 to deliver another series of pacing pulses in another attempt to deliver a T-shock. Alternatively, or after a predetermined number of attempts to deliver the T-shock, method 200 may be aborted at block 216 (as indicated by dashed line 240) or return to block 202 (as indicated by dashed line 242), immediately or at a later time, to re-determine the T-shock interval.

If a new T-shock interval is computed at block 224 and is different than the previously computed T-shock interval (computed at block 220), for example more than 20 ms greater than or less than the previously computed T-shock interval, method 200 may store the newly computed T-shock interval as the current T-shock interval and return to block 222. Another series of pacing pulses is delivered in an attempt to deliver a T-shock relative to the newly stored T-shock interval, without delivering a T-shock at the previously computed T-shock interval.

If the $T_p$ interval measurements during the second pacing pulse series are determined to be unstable at block 224, but the maximum signal quality threshold is not exceeded at block 226, the previously selected number of T-shocks may be adjusted at block 230. For example, if a nominal number of T-shocks was selected at block 213 based on a high signal quality during the first pacing pulse series, but the T-wave signal quality is determined to be lower during the second series of pacing pulses, the number of T-wave shocks may be increased at block 230. If the number of shocks was selected to be greater than the nominal number of shocks at block 218, the number of shocks may be unchanged or increased depending on the T-wave signal quality determined at block 224. For example if the T-wave signal quality was determined to be moderate during the first pacing pulse series and if the T-wave signal quality was determined to be low but still acceptable during the second series of pacing pulses, the selected number of shocks may be increased at block 230. In general, the number of T-wave shocks is not decreased from the original number of shocks scheduled at block 218 since the number of shocks scheduled at block 218 is based on the reliability of the $T_p$ interval measurements used to compute the T-shock interval. As such a variable number of T-wave shocks may be selected based on a signal quality parameter derived from the T-wave signals used to compute a T-wave shock interval and/or the signal quality of the T-wave signals sensed during a pacing pulse series delivered to synchronize a scheduled T-wave shock.

If sensing of intrinsic R-waves during the second pacing pulse series occurs, as determined at decision block 228, the scheduled T-shock may be withheld. Intrinsic R-wave sensing indicates a disruption in the stability of the paced rhythm. Another pacing pulse series may be delivered at block 222 in a second attempt to deliver the schedule T-shock. The next pacing pulse series may be delivered at adjusted pacing parameters (block 232). For example, if R-wave sensing occurs, the pacing pulse energy and/or pacing pulse rate may be increased to reduce the likelihood of intrinsic depolarizations from occurring during the pacing pulse series.

If no R-wave sensing occurs as determined at block 228, the scheduled T-wave shock is delivered at block 234 at the first offset relative to the computed T-shock interval. Blocks 222 through 234 are repeated until all of the selected number of T-wave shocks are delivered at the corresponding number of offsets relative to the computed T-wave shock interval, as determined at block 236. Method 200 is then terminated at block 238.

It is recognized that T-shocks may alternatively be delivered on the last pacing pulse of the initial pacing pulse series after computing the T-shock interval at block 214. Furthermore it is recognized that the T-wave signal quality analysis and T-shock interval computation could be performed during an intrinsic cardiac rhythm. The T-wave shock interval is computed relative to a sensed R-wave and T-wave shocks are delivered following a sensed R-wave at the computed T-wave shock (plus any desired offset).

The results of the T-shock tests may then be used in estimating the patient's defibrillation threshold. In one embodiment, the T-shocks are delivered at a shock pulse energy that is a safety margin below the maximum ICD output. If fibrillation is not induced, the T-shock energy is considered to be above the patient's ULV, indicating a high probability of successful defibrillation at the tested T-shock energy. However, it is recognized that additional testing may be performed by delivering T-shocks at the computed T-shock interval and predetermined offsets at varying shock energies. For example, the T-wave shock may be delivered at each offset from the computed T-shock interval using a shock energy set to a high level thought to be well above the patient's ULV. The T-shocks may then be repeated at successively lower energy levels until fibrillation is induced. The lowest energy that fails to induce fibrillation is determined as the patient's ULV and can be used in determining if the patient meets ICD implant requirements and in programming a defibrillation shock energy.

The number of pulses and offsets used relative to a T-shock interval may be predefined at fixed values corresponding to a signal quality threshold. Alternatively, the number of T-wave shocks may be determined as the number of pulses required between a minimum percentage and a maximum percentage of the T-wave shock interval when the shocks are spaced apart at predetermined fixed intervals. For example if a T-wave shock interval is 100 ms and the signal quality is determined to be poor, a variable number of T-wave shocks may be scheduled at 20 ms intervals extending from 60% to 140% of the T-shock interval. If the T-wave signal quality is determined to be high, a variable number of T-shock intervals extending from 80% to 120% of the T-shock interval at 20 ms intervals may be scheduled. It is recognized that numerous variations in implementing a variable number of T-shocks based on T-wave signal quality may be conceived by one having skill in the art and the benefit of the teachings provided herein.

Figure 7:
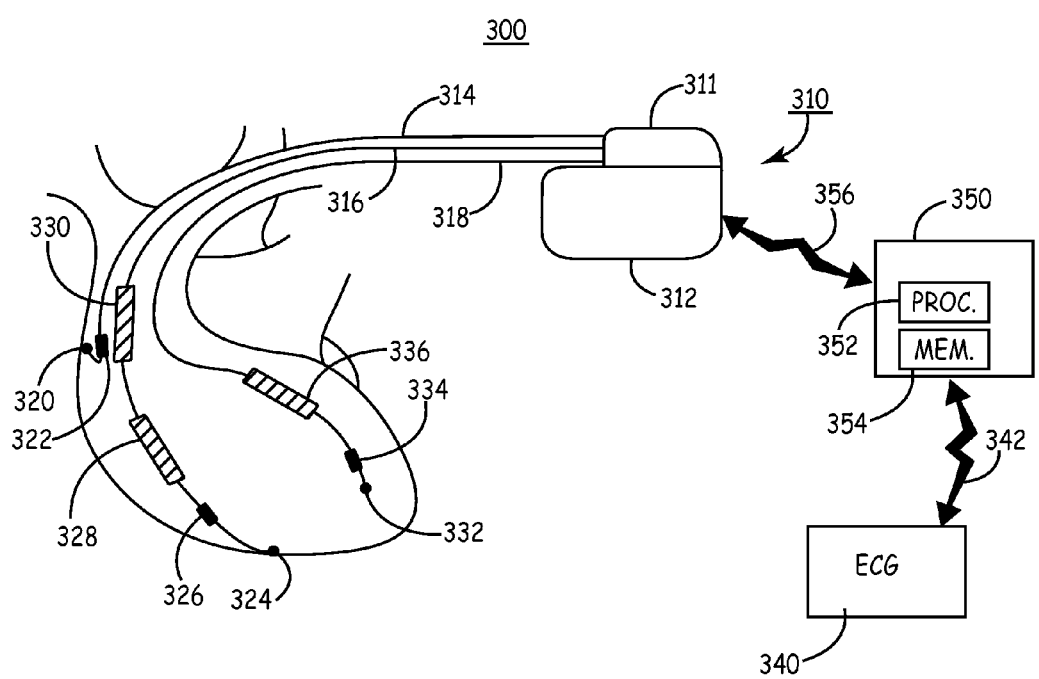
FIG. 7 is a schematic diagram of an alternative ICD system in which the present invention may be embodied.

FIG. 7 is a schematic diagram of an alternative ICD system 300 in which the present invention may be embodied. ICD 310, having housing 312 which can be used as a CAN electrode, is coupled via connector block 311 to a right atrial (RA) lead 314, a right ventricular (RV) lead 316, and a left ventricular (LV) lead 318. RA lead includes a RA tip electrode 320 and a RA ring electrode 322 for pacing and sensing in the right atrium. RV lead 316 includes a RV tip electrode 324 and a RV ring electrode 326 for pacing and sensing in the right ventricle. RV lead 316 further includes a RV coil electrode 328 and an SVC coil electrode 330. LV lead 318 includes an LV tip electrode 332, an LV ring electrode 334, and an LV coil electrode 336. According to various embodiments of the present invention, any of electrodes 320 through 336 and housing 312 may be selected for use in sensing T-wave signals for determining a T-wave shock interval and for analyzing the T-wave signal quality for determining a variable number of T-wave shocks to be delivered. Multiple sensing electrode configurations may be monitored sequentially or simultaneously for obtaining T-wave signal data for analyzing signal quality.

Furthermore, the pacing pulses delivered for determining a T-shock interval and prior to delivering a T-shock may be delivered using any available pacing electrodes. For example, a series of pacing pulses may be delivered using RV tip and ring electrodes 326 and 328 or using LV tip and ring electrodes 332 and 334.

In some embodiments of the invention, T-wave signals obtained using an external ECG leads, for example 12-lead ECG monitor 340, may also be analyzed for use in determining a variable number of T-wave shocks. ECG signals from a 12-lead ECG monitor 340 may be provided via a hardwired or wireless communication link 342 to an external programmer 350. Programmer 350 includes a processor 352 and memory 354 for storing and processing 12-lead ECG signals. In one embodiment, programmer 350 measures intervals between pacing pulses and T-wave signal peaks. A baseline T-wave shock interval is derived from the 12-lead ECG signals based on the occurrence of T-wave signal peaks relative to delivered pacing pulses (or QRS signals). This baseline T-wave shock interval may be communicated to ICD 310 via wireless communication link 356 and used by ICD 310 for verifying or adjusting a T-wave shock interval automatically computed by ICD 310. Alternatively, the baseline T-wave shock interval may be used in selecting a sensing configuration for timing T-wave shocks delivered by ICD 310 based on the sensing configuration that results in a T-wave shock interval that most closely matches the baseline interval.

The sensing configuration resulting in the smallest difference between the ECG baseline T-wave shock interval and a computed T-wave shock interval based on EGM sensing may be identified as the sensing configuration having the highest signal quality. The difference between the ECG-derived baseline T-wave shock interval and the EGM-derived T-shock interval may be used in selecting the number of T-wave shocks to be delivered.

Figure 8:
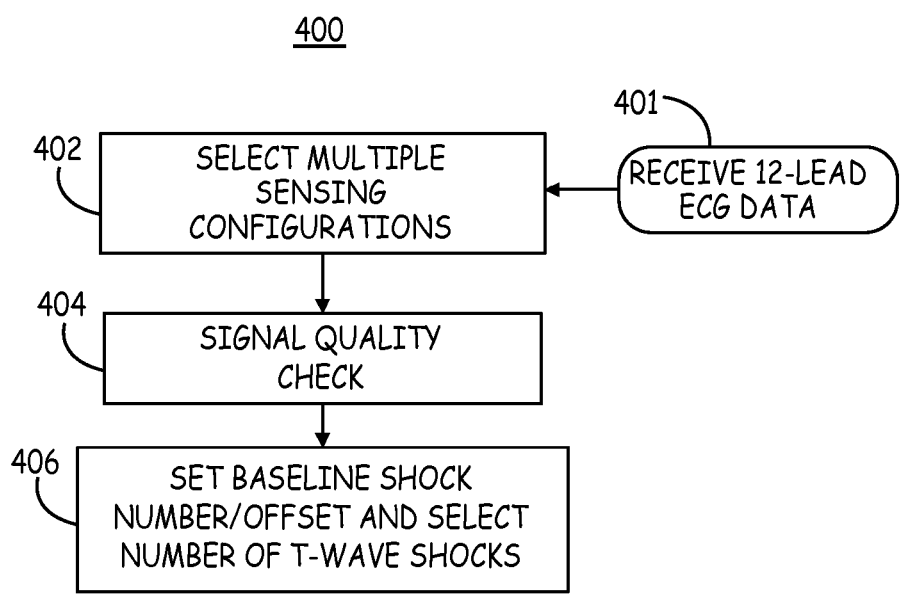
FIG. 8 is a flow chart of a method for selecting a variable number of T-wave shocks based on a comparative analysis of signal quality between different T-wave sensing configurations.

FIG. 8 is a flow chart of a method for selecting a variable number of T-wave shocks based on a comparative analysis of signal quality between different T-wave sensing configurations. At block 402, multiple sensing configurations may be selected from multiple electrodes available in an implanted ICD system. Additionally, 12-lead ECG data may be received from an external source at block 401. At block 404, a signal quality check is performed to determine a difference or variability between a magnitude and/or time interval of a T-wave signal fiducial point determined from the multiple sensing configurations or determine a T-wave morphology parameter indicative of the reliability of fiducial point detection. The T-wave signal fiducial point time interval may be a time interval used in computing a T-shock interval. As such, the signal quality check performed at block 404 may include comparing T-shock intervals computed for different sensing configurations and a baseline T-shock interval computed from the 12-lead ECG data. In some embodiments, a signal quality parameter determined from a single sensing configuration may be compared to the 12-lead ECG data to determine a relative level of signal quality.

At block 406, the number of T-wave shocks to be delivered during ULV testing is selected in response to the signal quality check at block 404. Greater variation between signal quality parameters determined for multiple sensing configurations or between an EGM sensing configuration and the 12-lead ECG data may result in a greater number of T-wave shocks being delivered.

Thus, a method and apparatus for delivering a variable number of T-wave shocks have been presented in the foregoing description with reference to specific embodiments. It is appreciated that various modifications to the referenced embodiments may be made without departing from the scope of the invention as set forth in the following claims.

The invention claimed is:

1. A method, comprising:
sensing a cardiac electrical signal;
determining a signal quality parameter of the cardiac electrical signal;
comparing the signal quality parameter to a signal quality threshold;
based on the comparison of the signal quality parameter to the signal quality threshold, determining a number of shock pulses for a shocking sequence including a plurality of shock pulses to be delivered to a patient's heart, wherein the number of shock pulses is determined to be a first number of shock pulses when the signal quality parameter is less than the signal quality threshold, and the number of shock pulses is determined to be a second number of shock pulses different than the first number of shock pulses when the signal quality parameter is greater than the signal quality threshold; and
scheduling the determined number of shock pulses to be delivered.

2. The method of claim 1 wherein the cardiac electrical signal comprises a plurality of T-wave signals, the signal quality parameter corresponds to a T-wave signal quality and the shock pulses are scheduled at a time corresponding to a T-wave signal.

3. The method of claim 2 wherein determining the signal quality parameter comprises determining a fiducial point for each of at least two T-wave signals.

4. The method of claim 3 wherein determining the signal quality parameter further comprises determining a difference between the determined fiducial points and wherein comparing the signal quality parameter to the signal quality threshold comprises comparing the difference to a signal quality threshold.

5. The method of claim 4, wherein the number of shock pulses is determined to be the first number of shock pulses when the difference is less than the signal quality threshold, and the number of shock pulses is determined to be the second number of shock pulses when the difference is greater than the signal quality threshold, wherein the second number of shock pulses is greater than the first number of shock pulses.

6. The method of claim 3 wherein the fiducial point corresponds to a time point of a feature of the T-wave signal.

7. The method of claim 3 further comprising determining a T-wave shock interval, wherein scheduling the determined number of shock pulses comprises scheduling each shock pulse at a unique offset relative to the T-wave shock interval.

8. The method of claim 7 wherein the T-wave shock interval is determined using a time point associated with one of the determined fiducial points.

9. The method of claim 7 further comprising:
delivering a series of pacing pulses;
sensing for intrinsic R-waves during delivery of the pacing pulse series;
delivering one of the determined number of shock pulses at the T-wave shock interval and a unique offset relative to the T-wave shock interval following a last pulse of the series of pacing pulses; and
withholding the one of the determined number of shock pulses if an intrinsic R-wave is sensed during delivery of the pacing pulses.

10. The method of claim 2 wherein scheduling the determined number of shock pulses comprises determining a fiducial point of a T-wave signal and determining a Twave shock interval in response to determining the fiducial point; and
wherein determining the signal quality parameter comprises determining a signal morphology parameter as an indication of the reliability of the determined fiducial point.

11. An implantable medical device, comprising:
electrodes for sensing a cardiac electrical signal and for delivering a shock pulse to a patient's heart;
a sensing module coupled to the electrodes for receiving the cardiac signal and analyzing the sensed signal for determining a signal quality parameter of the cardiac electrical signal and comparing the signal quality parameter to a signal quality threshold;
a shock pulse generating module coupled to the electrodes for delivering the shock pulse; and
a control module coupled to the sensing module and the shock pulse generating module and configured to, based on the comparison of the signal quality parameter to the signal quality threshold, automatically determine a number of shock pulses to be delivered to the patient's heart for a shocking sequence including a plurality of shock pulses, wherein the number of shock pulses is determined to be a first number of shock pulses when the signal quality parameter is less than the signal quality threshold, and the number of shock pulses is determined to be a second number of shock pulses different than the first number of shock pulses when the signal quality parameter is greater than the signal quality threshold;
the control module, sensing module, and shock pulse generating module configured to cooperatively deliver the scheduled determined number of shock pulses.

12. The device of claim 11 wherein the cardiac electrical signal comprises a plurality of T-wave signals, the signal quality parameter corresponds to a T-wave signal quality, and the control module controls the shock pulse generating module to deliver the shock pulses at times corresponding to the T-wave.

13. The device of claim 12 wherein, for determining the signal quality parameter, the sensing module determines a fiducial point for each of at least two T-wave signals.

14. The device of claim 13 wherein, for determining the signal quality parameter, the sensing module determines a difference between the determined fiducial points, and, for comparing the signal quality parameter to the signal quality threshold, the sensing module compares the difference to the signal quality threshold.

15. The device of claim 14 wherein the number of shock pulses is determined to be the first number of shock pulses when the difference is less than the signal quality threshold, and the number of shock pulses is determined to be the second number of shock pulses when the difference is greater than the signal quality threshold, wherein the second number of shock pulses is greater than the first number of shock pulses.

16. The device of claim 13 wherein the fiducial point corresponds to a time point of a feature of the T-wave signal.

17. The device of claim 12 wherein the control module is further configured to determine a T-wave shock interval and wherein the number of shock pulses each scheduled to be delivered at a unique offset relative to the T-wave shock interval.

18. The device of claim 17 wherein the T-wave shock interval is determined using a time point associated with one of the determined fiducial points.

19. The device of claim 18 further comprising:
a pacing pulse generating circuit for delivering a series of pacing pulses;
wherein the sensing module is further configured to sense for intrinsic R-waves during the pacing pulse series;
wherein the control module, sensing module and shock pulse generating module configured to cooperatively deliver one of the determined number of shock pulses at a time corresponding to the T-wave shock interval and a unique offset relative to the T-wave shock interval following a last pacing pulse of the series of pacing pulses and withhold the one of the determined number of shock pulses if an intrinsic R-wave is sensed during delivery of the pacing pulses.

20. The device of claim 12 wherein scheduling the determined number of shock pulses comprises determining a fiducial point of a T-wave signal and determining a Twave shock interval in response to determining the fiducial point; and
wherein determining the signal quality parameter comprises determining a signal morphology parameter as an indication of the reliability of the determined fiducial point.

21. A computer readable storage medium for storing a set of instructions which when implemented in a medical device system cause the system to:
analyze a cardiac electrical signal;
determine a signal quality parameter of the cardiac electrical signal;
compare the signal quality parameter to a signal quality threshold;
based on the comparison of the signal quality parameter to the signal quality threshold, determine a number of shock pulses for a shocking sequence including a plurality of shock to be delivered to a patient's heart, wherein the number of shock pulses is determined to be a first number of shock pulses when the signal quality parameter is less than the signal quality threshold, and the number of shock pulses is determined to be a second number of shock pulses different than the first number of shock pulses when the signal quality parameter is greater than the signal quality threshold; and
schedule the determined number of shock pulses to be delivered.

* * * * *

UNITED STATES PATENT AND TRADEMARK OFFICE
CERTIFICATE OF CORRECTION

PATENT NO. : 8,644,923 B2  
APPLICATION NO. : 12/178903  
DATED : February 4, 2014  
INVENTOR(S) : Paul A. Belk et al.

Page 1 of 1

It is certified that error appears in the above-identified patent and that said Letters Patent is hereby corrected as shown below:

In the Claims

Col. 15, line 23, delete "signal and determining a Twave shock" and insert in place thereof -- signal and determining a T-wave shock --;

Col. 16, line 38, delete "signal and determining a Twave shock" and insert in place thereof -- signal and determining a T-wave shock --;

Col. 16, line 44, delete "A computer readable storage medium" and insert in place thereof -- A computer-readable storage medium --;

Col. 16, line 55, delete "plurality of shock to be delivered" and insert in place thereof -- plurality of shock pulses to be delivered --.

Signed and Sealed this  
Fourteenth Day of April, 2015

Michelle K. Lee  
*Director of the United States Patent and Trademark Office*